(12) United States Patent
Reynolds et al.

(10) Patent No.: US 8,123,084 B2
(45) Date of Patent: Feb. 28, 2012

(54) RACK AND PINION DRIVE FOR BY-PASS CARTRIDGE

(75) Inventors: David L. Reynolds, Bromont (CA); Daniel MacDonald, Bromont (CA); Roger McCarthy, Brigham (CA)

(73) Assignee: Duoject Medical Systems Inc., Bromont, Quebec (CA)

( * ) Notice: Subject to any disclaimer, the term of this patent is extended or adjusted under 35 U.S.C. 154(b) by 0 days.

(21) Appl. No.: 12/737,013

(22) PCT Filed: Jun. 10, 2009

(86) PCT No.: PCT/CA2009/000806
§ 371 (c)(1),
(2), (4) Date: Nov. 30, 2010

(87) PCT Pub. No.: WO2009/149547
PCT Pub. Date: Dec. 17, 2009

(65) Prior Publication Data
US 2011/0068124 A1 Mar. 24, 2011

Related U.S. Application Data

(63) Continuation of application No. 12/157,866, filed on Jun. 13, 2008, now abandoned.

(51) Int. Cl.
*B67D 7/60* (2010.01)
(52) U.S. Cl. .......................... 222/390; 222/325; 604/209
(58) Field of Classification Search ................... 222/390, 222/391, 325–328, 145.5, 145.6, 386; 604/209, 604/191, 82–92
See application file for complete search history.

(56) References Cited

U.S. PATENT DOCUMENTS 2,725,877 A * 12/1955 Reiter et al. .................. 604/135
(Continued)

*Primary Examiner* — Lien Ngo
(74) *Attorney, Agent, or Firm* — Eric Fincham

(57) ABSTRACT

A device for mixing a substance comprised of two constituents contained in a cartridge (12) and having a cartridge holder (32) thereabout, the device comprising a plunger rod (46) for pushing a closure member (20) to permit the transfer of a diluent in a second chamber (28) through a by-pass channel (24) to mix with a constituent in a first chamber (26), the plunger rod (48) being driven by means of a rack (48) and a pinion gear (50) arrangement to prevent overly rapid movement of the plunger rod (46).

9 Claims, 7 Drawing Sheets

U.S. PATENT DOCUMENTS

| | | | |
|---|---|---|---|
| 4,226,236 A | * 10/1980 | Genese | 604/89 |
| 4,264,305 A | * 4/1981 | Rasmussen et al. | 433/90 |
| 4,968,299 A | * 11/1990 | Ahlstrand et al. | 604/90 |
| 5,505,704 A | * 4/1996 | Pawelka et al. | 604/191 |
| 6,599,272 B1 | * 7/2003 | Hjertman et al. | 604/209 |
| 2006/0069355 A1 | * 3/2006 | Judson et al. | 604/211 |

* cited by examiner

FIG. 8
FIG. 9
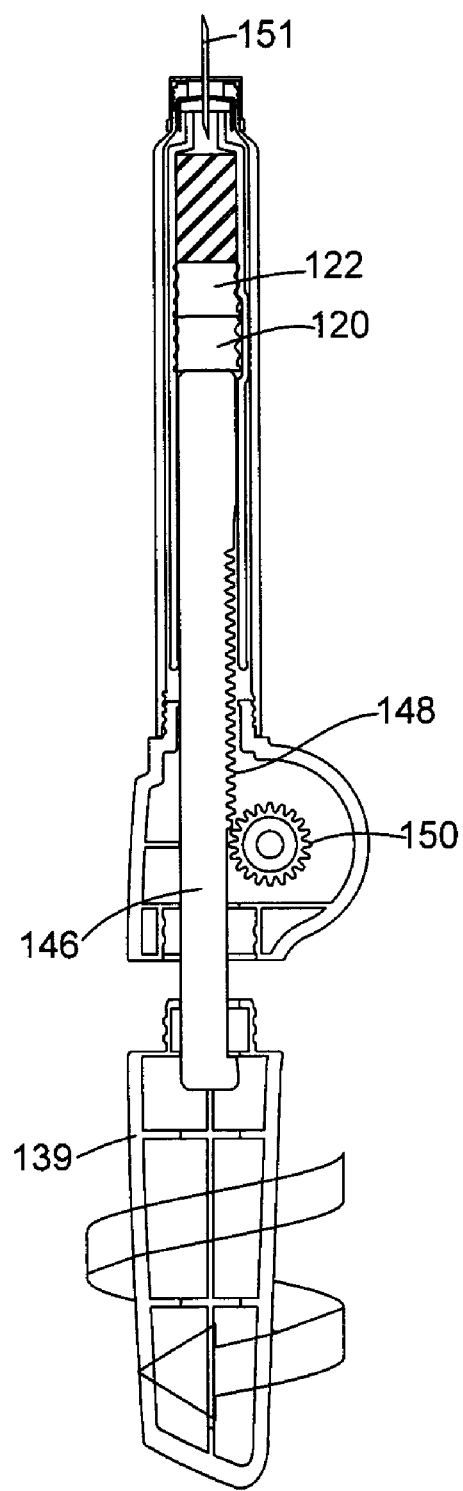
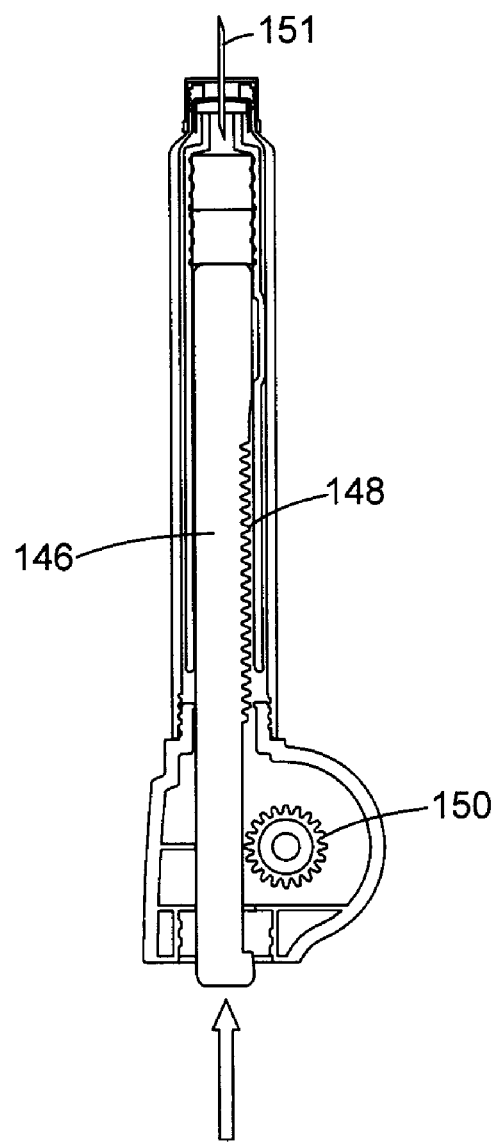

RACK AND PINION DRIVE FOR BY-PASS CARTRIDGE

This application claims benefit of, incorporates by reference, and priority from a 371 of PCT/CA 2009/000806, filed Jun. 10, 2009, which is a Continuation of U.S. patent application Ser. No. 12/157,866, filed Jun. 13, 2008, and now abandoned.

FIELD OF THE INVENTION

The present invention relates to a by-pass cartridge and in particular to a device and method for storing, mixing and delivering pharmaceuticals.

BACKGROUND OF THE INVENTION

In pharmaceutical delivery systems, it is sometimes necessary to mix a drug in powder form with a diluent in order to be able to deliver the drug to a subject. This can be done manually by injecting the diluent into a vial containing the powdered drug, mixing the drug into the diluent and aspirating the drug in fluid form into a syringe for subsequent injection into the subject. Such manual procedures are generally considered to be cumbersome and inconvenient and often lead to wastage of some of the drug as it may remain in the vial.

Also known in the art are dual chambered syringes which use a by-pass channel to provide fluid communication between the two chambers. The two chambers are commonly defined within a syringe barrel by two separate pistons and an end stopper spaced apart within the syringe barrel. In such an arrangement, the two chambers are placed in fluid communication by the by-pass channel by actuation of the outer most piston within the syringe barrel. This causes both pistons within the syringe barrel to advance to a point where the inner most piston becomes aligned with the by-pass channel. At that point, further actuation of the outer most piston causes fluid contained in the chamber between the two pistons to flow into the outwardly extending by-pass channel and around the inner most piston which remains stationary.

With the two chamber syringe barrel and external by-pass arrangement described above, a danger exists in the possibility that the inner most piston is pushed too far along such that it goes past the by-pass channel before full transfer of the diluent occurs. This may be caused by an overly vigorous application of the plunger to the outer most piston. Once the inner most piston is pushed past the by-pass channel without having allowed proper fluid flow from the first chamber to the second chamber, it can be extremely difficult to correct.

With some pharmaceutical constituents, in order to properly constitute the pharmaceutical substance, it is desirable to ensure that the mixing of the two constituents occurs slowly and evenly.

SUMMARY OF THE INVENTION

It is an object of the present invention to provide a method and a device which allows the mixing of two constituents of a pharmaceutical substance and which overcomes the above drawbacks in prior art devices.

According to one aspect of the present invention, there is provided a device for mixing a substance comprised of two constituents, the device comprising a cartridge, a cartridge holder, a tubular container having a fluid communication end and an actuation end, the fluid communication end being receivable in the cartridge holder, the tubular container having a first closure member disposed at the fluid communication end, a second closure member disposed at the actuation end, a piston within the container intermediate the first and second closure members, and a by-pass channel for enabling fluid to by-pass the piston when the piston is in the by-pass position, a plunger rod engageable with the second closure member for moving the second closure member within the container, the plunger rod having a rack gear formed thereon, a housing, a pinion gear mounted within the housing, the pinion gear being engageable with the rack gear, and a handle connected to the pinion gear.

The transfer device of the present invention may be utilized with any suitable by-pass type cartridge or container. Many such by-pass cartridges or containers are known in the art. Conventionally, the second closure member is screw threadedly connectable to the plunger rod.

Utilizing the transfer device of the present invention significantly reduces the possibility of the piston moving past the by-pass channel prior to transfer of the diluent to the chamber containing the active ingredient. In other words, it becomes difficult to rapidly move the second closure at the actuation end.

BRIEF DESCRIPTION OF THE DRAWINGS

Having thus generally described the invention, reference will be made to the drawings illustrating an embodiment thereof, in which:

FIG. 8 is a cross-sectional view illustrating removal of the cover for access to the plunger rod; and FIG. 9 is a cross-sectional view showing the final step of the operation.

DETAILED DESCRIPTION OF THE INVENTION

Figure 1:
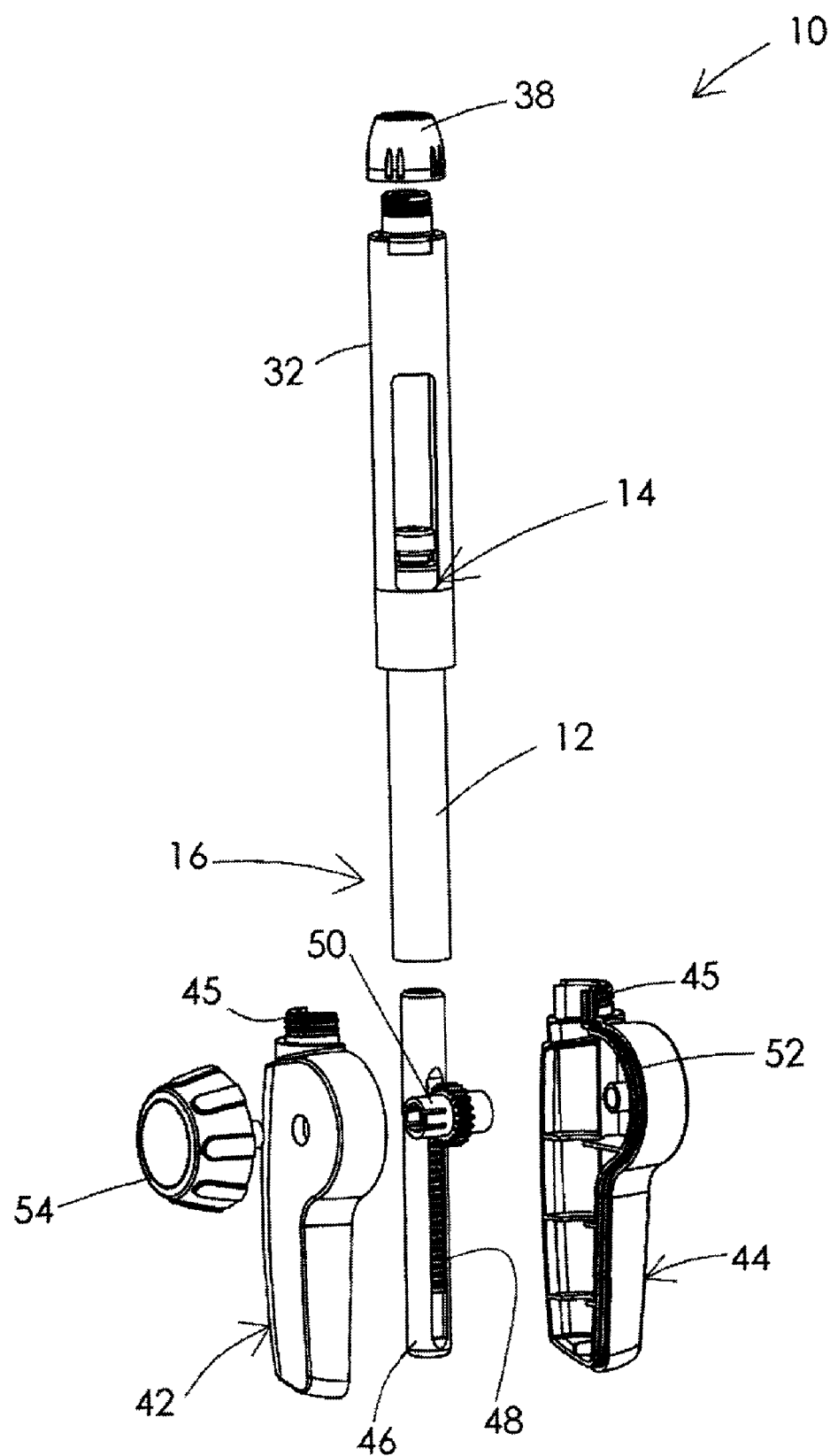
FIG. 1 is a partially exploded perspective view of a device according to the present invention.
Figure 2:
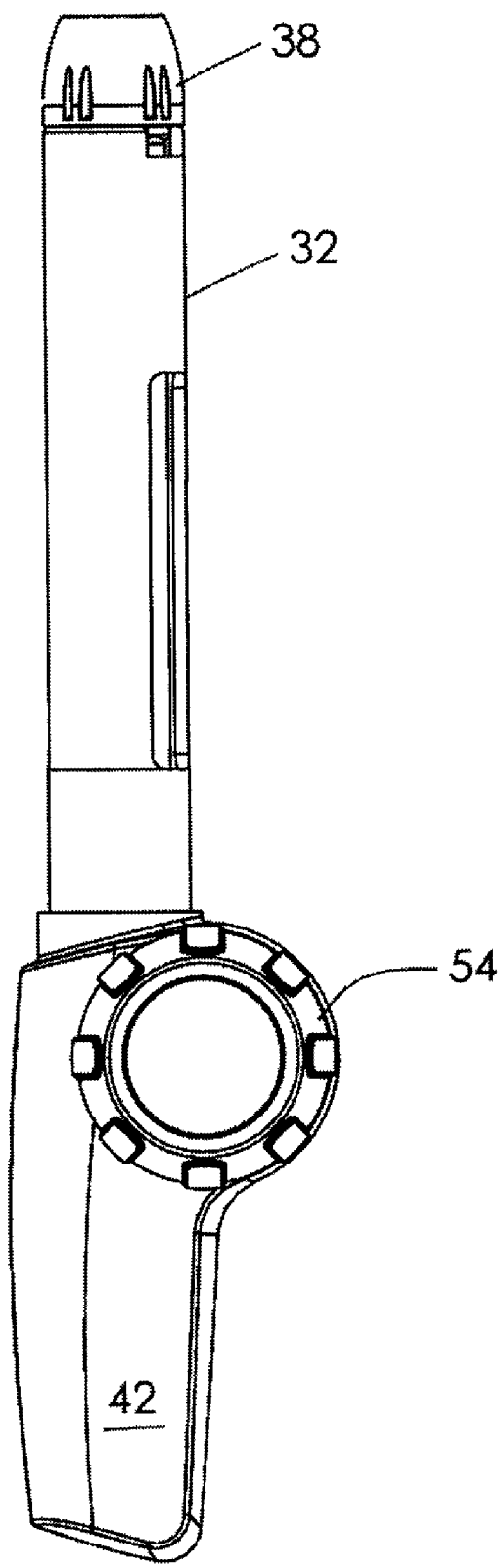
FIG. 2 is a side elevational view of the device.

Referring to the drawings in greater detail and by reference characters thereto, there is illustrated an assembly generally designated by reference numeral 10 and which assembly 10 includes a cartridge 12. Cartridge 12 is of a substantially conventional structure and includes an activation end 16 and a fluid communication end 14. A first closure member 18 seals fluid communication end 14 while a second closure member 20 seals activation end 16.

Situated interiorly of the cartridge 12 and intermediate closure members 18 and 20 is a plunger 22 which divides the cartridge into a first chamber 26 and a second chamber 28. As is known in the art, a by-pass 24 provides fluid communication between first chamber 26 and second chamber 28. Normally, first chamber 26 will carry the dry pharmaceutical component to be reconstituted while second chamber 28 normally will carry a liquid diluent. Naturally, other arrangements such as two liquids can be utilized.

At it's upper end (fluid communication end) cartridge 12 has a shoulder 30.

Cartridge holder 32 surrounds cartridge 12 and has screw threads 31 at its lower end. A shoulder 36 of cartridge holder 32 abuts shoulder 30 of cartridge 12.

A cap 38 having screw threads thereon is arranged to fit on fluid communication end 14 of cartridge 12. Cap 38 includes a piercing member 40 which has a passageway 43 therein. A gas permeable hydrophobic membrane 41 is secured to the top of cap 38 and covers passageway 43.

Assembly 10 includes a pair of half housings 42 and 44 which are secured together. At their upper ends, housings 42 and 44 have external threads 45 designed to engage with threads on the inner bottom wall of cartridge holder 32.

Interiorly of housing 42, 44 is a plunger rod 46 which has a rack gear 48 formed on one side thereof. Rack gear 48 is designed to engage with a pinion gear 50. A gear retainer 52 is formed on one side of housing 44 while a wheel 54 is arranged to drive pinion gear 50.

Figure 3A:
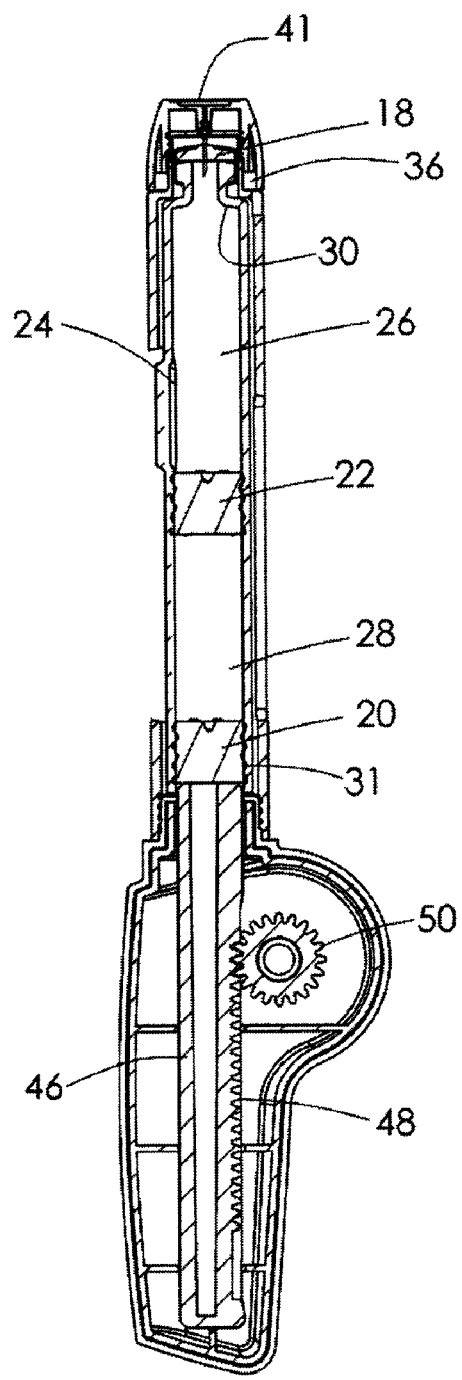
FIGS. 3A, 3B and 3C are side sectional view illustrating operation of the device.
Figure 3B:
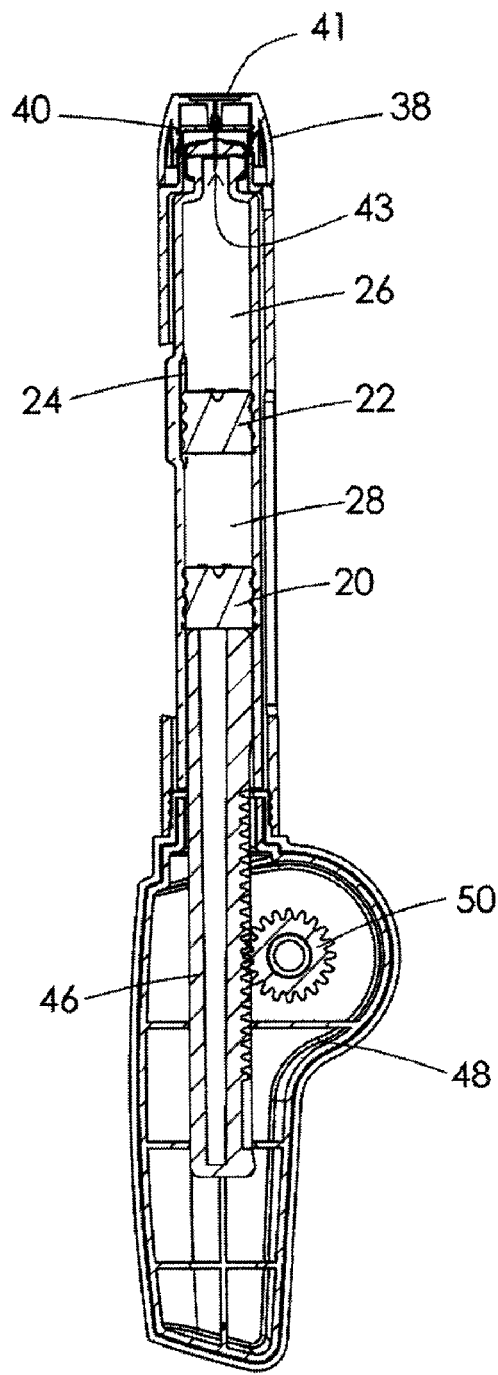
Figure 3C:
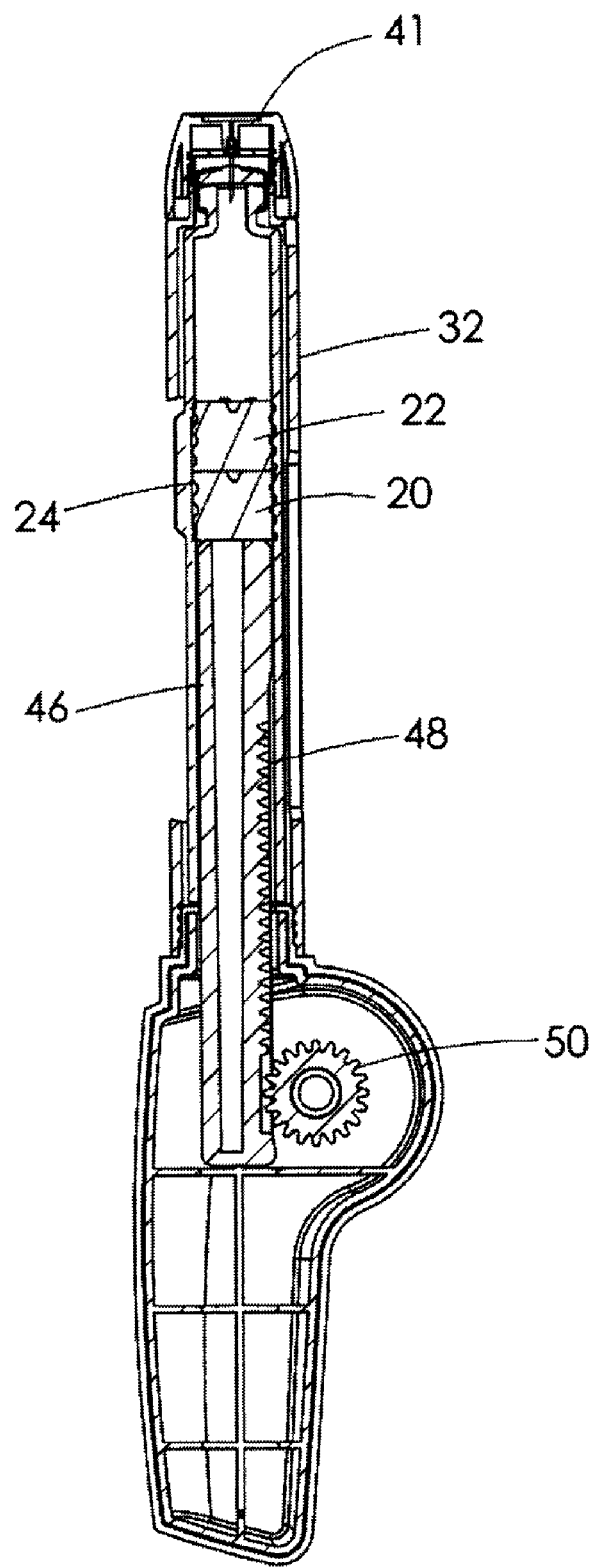

In operation, and as may be seen in FIGS. 3A to 3C, housing 42, 44 is screw threadedly engaged with cartridge holder 32. At this point in time, plunger rod 46 abuts closure member 20. Operation of wheel 54 will cause movement of plunger rod 46 which will then advance closure member 20 which in turn causes pressure to advance plunger 22 to the position shown in FIG. 3B wherein it is located at by-pass 24. Continued slow and steady advancement will then cause the diluent in second chamber 28 to enter first chamber 26 until closure member 20 abuts plunger 22. The two components in chambers 26 and 28 are then mixed; any air present is evacuated through passageway 43 in piercing member 40 while the liquid is retained due to hydrophobic membrane 41.

Figure 4:
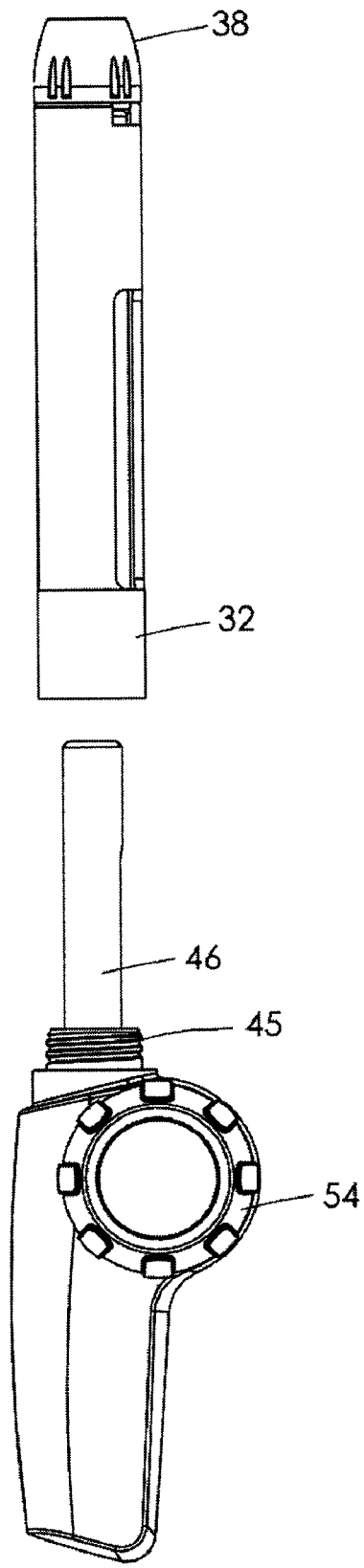
FIG. 4 illustrates the detachment of the cartridge holder from the housing.
Figure 5:
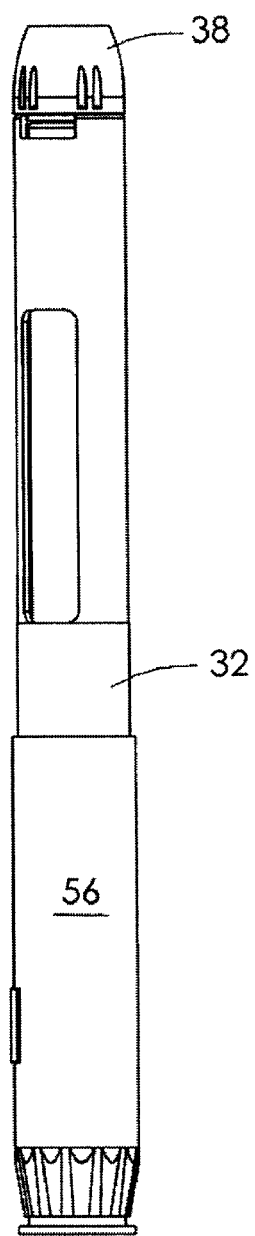
FIG. 5 illustrates a pen injector utilizing the cartridge of the present invention.
Figure 6:
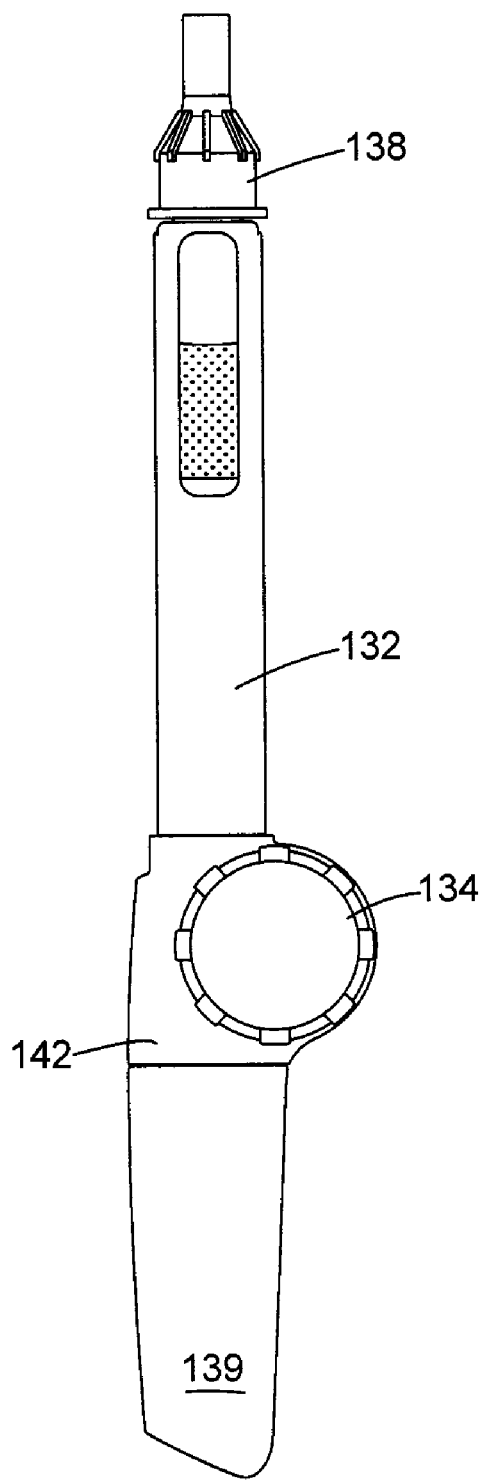
FIG. 6 is a side view of a further embodiment of the present invention.
Figure 7:
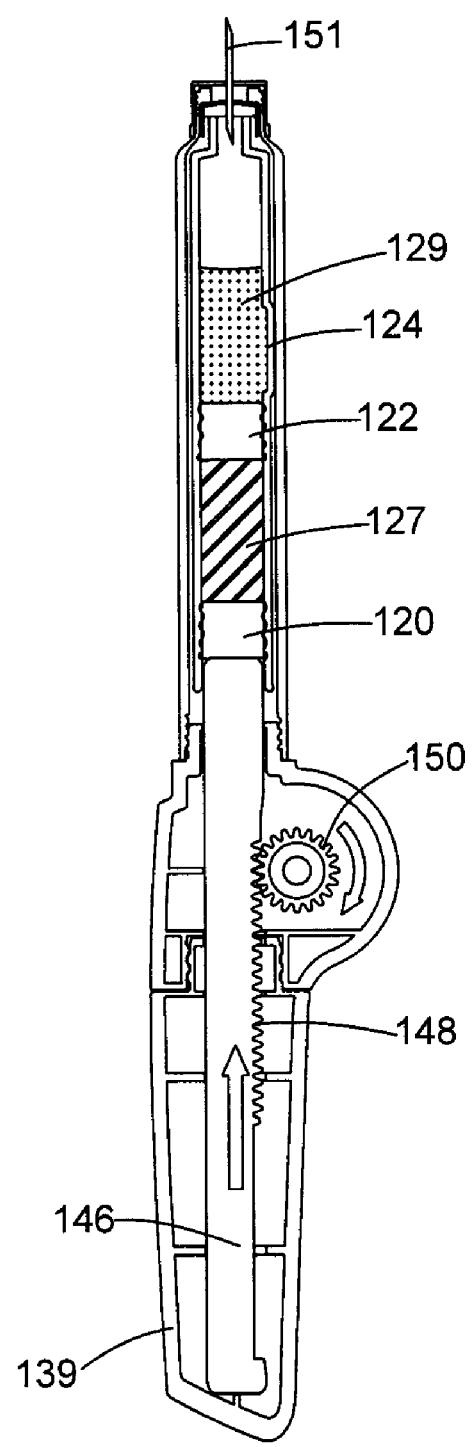
FIG. 7 is cross-sectional view of the device of FIG. 6 illustrating operation thereof.

When fully mixed, cartridge holder 32 can be unscrewed from housing 42, 44 and is then attached to a pen injector 56 in a conventional manner as shown in FIGS. 4 and 5.

Turning to the embodiment of FIGS. 6 to 9, reference numerals in the 100's are used for the components which are similar to those of the previously described embodiment. In this embodiment, there is provided a housing 142 which is not as elongated as the housing of the previous embodiment. Instead, there is provided a cover 139 which is screwthreadedly engaged with housing 142.

As in the previous embodiment, there is provided a plunger 122 to separate a solid portion 129 and a diluent 127. A bottom closure 120 is provided.

There is also provided a plunger rod 146 having a rack gear 148 on one side thereof. Pinion gear 150 is operatively engaged with rack gear 148 and by means of a wheel 154, pinion gear 150 is driven as indicated by the arrows.

The arrangement is such that the length of the rack gear 148 permits driving of the plunger rod 146 to an extent as shown in FIG. 8 wherein the substances in the two compartments have been mixed. Subsequently, cover 139 may be removed as indicated by the arrow and access gained to plunger rod 146 which may then be pushed by the user as shown in FIG. 9 to inject the active ingredients. This arrangement thus provides for an assurance that all the diluent is mixed with the drug while permitting a conventional injection by means of needle 151.

We claim:

1. A device for mixing a substance comprised of two constituents, the device comprising:
   a cartridge (12);
   a cartridge holder (32);
   said cartridge having a fluid communication end (14) and an actuation end (16), said fluid communication end (14) being receivable in said cartridge holder (32), said cartridge having a first closure member (18) disposed at the fluid communication end, a second closure member (20) disposed at the actuation end (16), a piston (22) within the cartridge intermediate the first and second closure members, and a by-pass channel (24) for enabling fluid to by-pass the piston (22) when the piston is in a by-pass position;
   a plunger rod (46) engageable with the second closure member (20) for moving the second closure member (20) within the cartridge, said plunger rod having a rack gear (48) formed thereon, said rack gear (48) having a length to permit said plunger rod (46) to advance said second closure member (20) only to proximate said by-pass channel (24);
   a housing (42), a pinon gear (50) mounted within said housing, said pinon gear (50) being engageable with said rack gear (48), and a handle (54) connected to said pinion gear.

2. The device of claim 1 further including a cap (38) at a distal end of said cartridge (12), said cap (38) having a piercing member (40) with a fluid passageway (43) therein, and a hydrophobic membrane (41) associated with said passageway (43) to permit the egress of gas therethrough while preventing the passage of liquid.

3. The device of claim 1 wherein said handle comprises a thumb wheel (54), the arrangement being such that a turning of said thumb wheel (54) drives said pinon gear (50) which in turn drives said rack gear (48) to advance said plunger rod (46).

4. The device of claim 3 wherein said housing (42) is screw threadedly engaged with said cartridge holder (12).

5. The device of claim 2 wherein a first chamber (26) is defined between said first closure member and said piston (22) and a second chamber (28) is defined between said second closure member (20) and said piston (22), said first chamber (26) containing a dry constituent and said second chamber (28) containing a diluent therefore.

6. The device of claim 2 wherein said hydrophobic membrane (41) is secured to a top of said cap, said hydrophobic membrane extending over said passageway (43).

7. The device of claim 2 wherein said cap (38) is screw threadedly engaged with said cartridge holder (32).

8. The device of claim 1 further including a cover (139) removably connected to said housing (142), said plunger rod (146) being accessible to a user when said cover (139) is removed.

9. The device of claim 8 wherein said rack gear (148) has teeth extending through only a portion of the length of said plunger rod (146), the arrangement being such that when said rack gear (148) does not engage with said pinion gear (150), said plunger rod (146) may be pushed manually.

\* \* \* \* \*